United States Patent [19]
Morrison

[11] 3,962,046
[45] June 8, 1976

[54] METHOD AND APPARATUS FOR TESTING PROPERTIES OF LIQUIDS

[75] Inventor: Charles Alfred Morrison, Isleworth, England

[73] Assignee: George Kent Limited, Luton, England

[22] Filed: July 24, 1974

[21] Appl. No.: 491,511

[30] Foreign Application Priority Data
July 27, 1973   United Kingdom............... 35797/73
Nov. 26, 1973   United Kingdom............... 54777/73

[52] U.S. Cl................................. 204/1 T; 73/1 G;
73/19; 204/195 R; 417/108
[51] Int. Cl.²....................................... G01N 27/46
[58] Field of Search.................. 73/19, 23, 1 R, 1 G;
23/230 R, 230 A, 232 R, 253 A, 254 R;
204/195 R, 195 P, 195 M, 1 Y, 1 T; 417/108;
251/5

[56] References Cited
UNITED STATES PATENTS

| | | | |
|---|---|---|---|
| 3,272,725 | 9/1966 | Garst............................. | 204/195 P |
| 3,374,743 | 3/1968 | Stutely et al.................... | 417/65 |
| 3,485,472 | 12/1969 | Bozich............................ | 251/5 |
| 3,495,438 | 2/1970 | Mangum.......................... | 73/19 |
| 3,552,712 | 1/1971 | Whitlock......................... | 251/5 |
| 3,560,111 | 2/1971 | Sterlini........................... | 417/65 |
| 3,661,010 | 5/1972 | Neuwelt........................... | 73/19 X |
| 3,672,790 | 6/1972 | White et al...................... | 417/108 |
| 3,718,407 | 2/1973 | Newbrough....................... | 417/108 |
| 3,738,154 | 6/1973 | Henry............................. | 73/19 |

Primary Examiner—Richard C. Queisser
Assistant Examiner—Stephen A. Kreitman
Attorney, Agent, or Firm—Browdy and Neimark

[57] ABSTRACT

Apparatus for measuring the dissolved oxygen content of water comprises an open-ended duct immersed in the water in an upright position, an oxygen-detecting probe in the lower end portion of the duct, and means for injecting a continuous stream of air into the upper portion of the duct, the air causing water to rise in the duct and thereby induce a flow of water into the duct and past the probe. A valve in the upper end of the duct is operable by compressed air to shut off the top of the duct so that air builds up inside the duct and back-flushes the liquid through a strainer on the lower end of the duct. Displacement of the water around the duct by air enables the probe to be calibrated. The upper section of the duct into which air is injected may be connected to the lower section containing the probe by polyethylene tubing of a length to enable the lower section of the duct to be lowered to any desired depth.

4 Claims, 2 Drawing Figures

METHOD AND APPARATUS FOR TESTING PROPERTIES OF LIQUIDS

This invention relates to apparatus for measuring a property of a liquid by means of a probe immersed in the liquid and responsive to variation in the property being measured.

In many applications in which a probe is used to measure a property of a liquid, it is necessary to cause the liquid to flow past the probe to prevent the probe being fouled by waterborne deposits and to ensure that the sample being tested by the probe is representative of the mass of the liquid.

This is particularly the case in the measurement of the dissolved oxygen content of water in rivers, reservoirs or sewage plants by means of an electro-chemical probe. A probe of this kind is described in British Patent Specification No. 999,909. This probe, which is immersed in the water under test, includes a membrane permeable to oxygen but not to the water and means by which the content of oxygen permeating the membrane may be ascertained. This sensitive membrane is particularly subject to fouling by suspended solids, waterborne deposits, algae and other biological growths. These deposits reduce the area and/or permeability of the membrane and result in false readings of oxygen content. It is not practicable to clean the membrane automatically by a brush or wiper actuated by electrical or pneumatic means since the membrane is of thin and comparatively fragile plastics material which would be readily damaged by a cleaner involving physical contact. It is therefore preferable to prevent adhesion of the possible fouling agents by vigorously agitating the sample of liquid in the immediate vicinity of the probe.

Known methods employed for this purpose include paddles, propellers, and other rotary devices driven by electric motors either submerged or located above liquid level. Apart from the obvious disadvantage of having electrical apparatus in wet location, rotary devices are liable to become entangled with weeds and other debris. Moreover they are not easily made effective with cylindrical probes such as that described in the above mentioned British Pat. specification No. 999,909. Reciprocating and semi-rotary devices driven by compressed air must similarly be sealed against ingress of liquid and the moving parts protected against clogging and wear by mud and grit in suspension.

The problem of ensuring that a sample of liquid being tested by a probe is representative of the mass of liquid from which the sample was obtained is particularly important in oxygen measurement by an electro-chemical probe since the presence and operation of the electrochemical system itself may modify the oxygen content of the liquid in the immediate vicinity of the probe. It is therefore essential that the sample in contact with the probe be changed with a frequency sufficient to avoid any substantially erroneous readings, and in the case of a probe of the kind described in British Pat. specification No. 999,909 velocities of water flow of the order of 10 cms. per second are usually recommended.

The object of the invention is to provide a method and apparatus for measuring a property of the liquid, which is not subject to the disadvantages of the electrical or pneumatic devices referred to above.

According to the present invention there is provided a method of measuring a property of a liquid by means of a probe responsive to variation in said property, comprising locating the probe in an open-ended duct having at least a portion thereof immersed in the liquid and extending continuously upwards towards one end of the duct, and injecting a gaseous fluid into said portion of the duct so as to cause the gaseous fluid, during passage upwards in the said portion of the duct, to entrain liquid in the duct and discharge the liquid through said one end of the duct, whereby a continuous stream of the liquid flows past the probe. The upper end of the duct may be immersed in the liquid, or spaced above the surface of the liquid by a distance small enough to ensure that the liquid entrained by the gaseous fluid is discharged from the duct.

In the method of the invention, the continuous discharge of liquid from the upper end of the duct causes fresh liquid to flow continuously into the duct through the other end and into contact with the probe in the duct. The rate of flow of liquid through the duct is preferably high enough to effect a useful degree of automatic cleaning of the membrane. The gaseous fluid can conveniently be compressed air, and in this case it would of course be essential to place any oxygen measuring probe upstream of the point at which the air is injected into the duct.

The method of the invention thus has the advantage that liquid is induced to flow past the probe without the aid of any moving parts immersed in the liquid.

According to the invention there is also provided apparatus for measuring a property of a liquid, comprising an open-ended duct for flow therethrough of a sample of the liquid to be measured, a probe responsive to variation in said property mounted in the duct, and a pump for pumping the sample through the duct, characterized in that the apparatus is adapted to be mounted with at least a portion of the duct immersed in the liquid and extending continuously upwards towards one end thereof, and the pump comprises injector means operable to inject gaseous fluid into said portion of the duct to entrain liquid in the duct and discharge the liquid through said one end of the duct. The section of the duct containing the probe is preferably designed to provide the maximum velocity and turbulence in the flow of liquid past the probe.

The apparatus of the invention includes a shut-off valve operable to close the duct at or adjacent said one end thereof, whereby continued injection of the gaseous fluid into the duct cause back-flushing of the liquid in the duct out the other end thereof. The back-flushing will have a cleaning action on the probe and duct, particularly in the case where the inlet to the duct is fitted with a strainer, and in addition back-flushing of the liquid out of the duct by gaseous fluid having known properties to which the probe is responsive enables the apparatus to be calibrated on site by co-relating the output of the probe with the known properties of the gaseous fluid when the gaseous fluid has displaced the liquid from around the probe.

Apparatus suitable for measuring the oxygen content in static water in for example a sewage plant, in accordance with the present invention, will now be described by way of example with reference to the accompanying drawings, in which.

Figure 1:
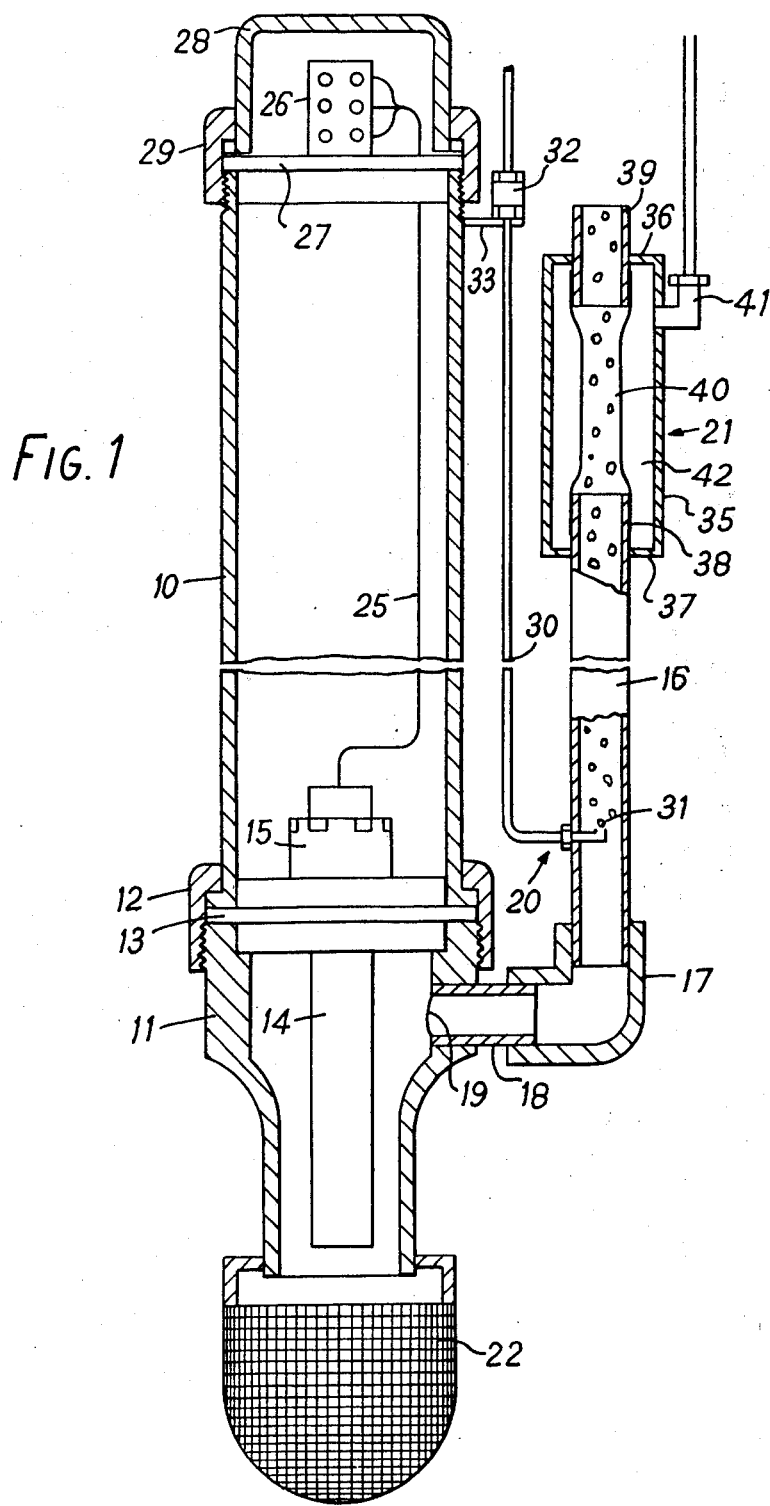
FIG. 1 is a sectional elevation view of the apparatus.

The apparatus shown in FIG. 1 comprises a vertical support tube 10, a tubular skirt 11 secured by a locking ring 12 to the lower end of the tube 10, a sealing plate 13 clamped between the lower end of the tube 10 and the skirt 11 and closing off the lower end of the tube 10, an oxygen responsive probe 14 secured by a compression nut 15 in an aperture in the plate 13, the probe extending downwards into the skirt, a standpipe 16 arranged alongside the support tube 10, the lower end of the standpipe being connected by an elbow joint 17 to a short stub tube 18 mounted in a port 19 in the side wall of the skirt, an air injector 20 for injecting air under pressure into the lower end of the standpipe, and a shut-off valve 21 for closing the upper end of the standpipe. The open lower end of the skirt 11 is fitted with a strainer 22 consisting of a wire or plastic mesh screen. The electrical output from the probe 14 is fed by a cable 25 extending upwards within the support tube 10 to a terminal block 26 from which cable connections for remote indicating or recording equipment are made. The terminal block is mounted on a plate 27 clamped between the upper end of the support tube and a cover 28 which protects the terminal block, the cover being secured on the support tube by a locking ring 29. The support tube, skirt, standpipe and other components can conveniently be manufactured in a polyvinylchloride or similar plastics material.

The air injector 20 consists of a length of small bore pipe 30 which extends downwards alongside the support tube 10 and enters the standpipe 16 through an opening in the wall thereof adjacent its lower end, the pipe 30 terminating in a smaller diameter jet or orifice 31 restricting flow of air through the pipe. The upper end of the pipe 30 is fitted with a coupling 32 mounted on a bracket 33 on the support tube and adapted to connect the pipe 30 to a supply of air or other gas under pressure, the coupling 32 being at a level above the surface of the water when the apparatus is in use.

The shut-off valve 21 is mounted on the upper end of the standpipe and consists of an outer casing 35 having aligned apertures in its top and bottom walls 36, 37, the upper end portion 38 of the standpipe being sealed in the aperture in the bottom wall 37 and an outlet pipe 39 being sealed in the aperture in the top wall 36, a collapsible tubular member 40 of rubber or similar elastic material mounted on the upper end portion 38 of the standpipe and on the outlet pipe 39, and a connection 41 for supplying air under pressure to the interior of the casing 35. The interior of the casing thus forms an air-tight valve chamber 42 which encloses the tubular member 40 so that the tubular member can be collapsed to close the upper end of the standpipe by supplying air under pressure to the valve chamber through the air connection 41, and the standpipe then opened by venting the valve chamber so that the member 40 will resume its tubular shape.

In use the apparatus is partially immersed in the water to be tested to a depth such that the top of the outlet pipe 39 is a few centimeters above the surface of the water and, when the valve chamber 42 is vented to atmosphere through the air connection 41 so that the shut-off valve is open, the water enters the skirt 11 through its open lower end and fills the standpipe to the level of the surrounding water. When air under pressure is supplied to the pipe 30, the air is ejected from the jet 31 as a stream of bubbles which rises to the surface of the liquid in the standpipe. The consequent reduction in density of the column of water in the standpipe induces liquid to flow into the bottom of the standpipe through the skirt 11 and elbow joint 17 while an equal quantity is displaced at the top on the well-known principle of the air-lift pump, eventually overflowing from the outlet pipe 39 into the main mass of liquid. The air supplied through pipe 30 thus induces a continuous flow of water into the skirt 11 and out through the standpipe 16, and the oxygen content of the water flowing through the annular space between the probe and the skirt is continuously measured by the probe. The standpipe can conveniently have a nominal internal diameter of one centimeter. The skirt 11 may be dimensioned and profiled to increase the velocity of flow past the probe and cause turbulence. For this purpose, the lower open end of the skirt is reduced in diameter to provide a comparatively small cross sectional area between the probe and the skirt and thereby cause a high velocity of flow past the probe. The increase in diameter of the skirt in the direction of flow towards the upper end thereof causes turbulence in the flow of water and the sudden change in direction of the flow into the port 19 in the side wall of the skirt also increases the turbulence.

It will be seen that since the air or other gas enters the flow of water through the apparatus at a point downstream from the probe, the output of the probe is not affected by the presence of the air or gas in the flow stream. The discharge of gasified water from the outlet pipe 39 will not normally interfere with the probe measurement due to the large volume of water in which the apparatus would normally be used. The gasified liquid may however be taken to a remote point by a flexible tube connected to the outlet pipe 39 in a case in which the volume of water being tested was small.

The strainer 22 on the skirt prevents leaves and other relatively large debris blocking flow of water through the apparatus or fouling the probe. Where the quantity and nature of the solid matter is such that the strainer itself may eventually become blocked, the shut-off valve 21 is closed temporarily by supplying air under pressure to the valve chamber 42, while continuing to supply air through the pipe 30. The air then accumulates in the standpipe and causes a backflow of water, and eventually air, through the strainer to clear away the debris. Supply of pressurized air to the valve chamber 42 can conveniently be controlled by an electrically operated control device arranged such that when the control device is de-energized the valve chamber is vented to atmosphere so as to open the valve, and when the device is electrically engerzied the air supply is applied to the valve chamber to close the valve. The energizing and de-energizing cycle of operations may be controlled by a timing mechanism of known type, either of electrical, pneumatic or clockwork operation.

Alternatively, or in addition, the procedure of closing the valve 21 may be used as a method of calibrating or checking the correct functioning of the probe. In a case where air is being used as the gaseous fluid injected into the standpipe, and the probe is adapted to measure the oxygen content of the water being tested, when the valve 21 is closed the air will accumulate in the standpipe and eventually pass over the probe, thereby causing the probe to provide its maximum output. Failure of the indicator or recorder connected to the electronic amplifier used with the probe to register an appropriate reading will indicate the necessity of adjustment of the amplifier or replacement of the probe.

The apparatus shown in FIG. 1 is for use on sites where a supply of air under pressure is available, as is frequently the case in sewage plants. The consumption of air is however very small and the apparatus may include small electrically driven air compressors where no external supply of air is available or where it is desired to take only an electrical cable to the apparatus.

Figure 2:
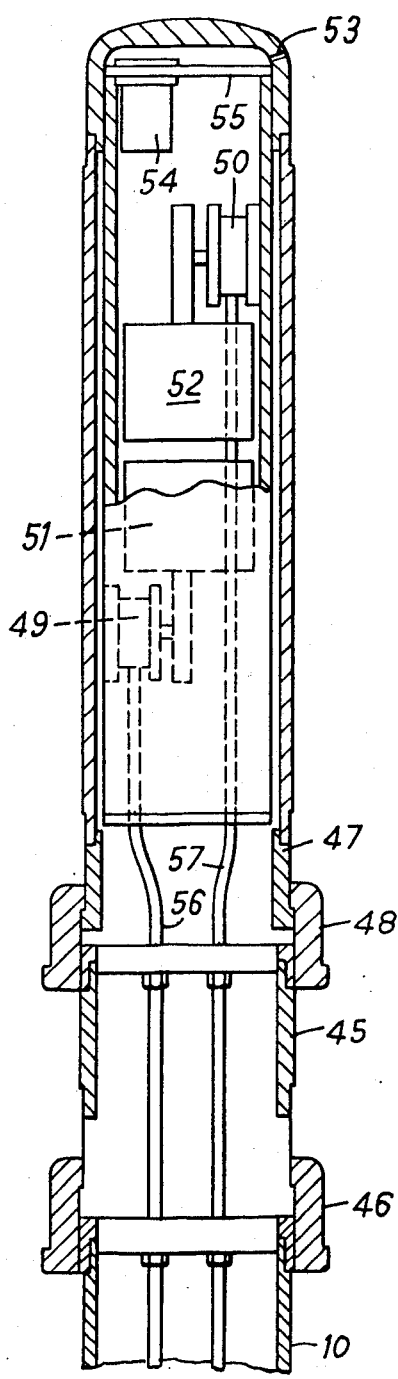
FIG. 2 is a sectional elevation view of part of a modified construction of the apparatus of FIG. 1.

FIG. 2 shows a modification of the apparatus of FIG. 1 in which the cover 28 is replaced by a tubular extension piece 45 secured on the top of the support tube 10 by a locking ring 46, and an enlarged cover 47 secured on top of the extension piece 45 by a further locking ring 48. The extension piece 45 houses the cable terminal block, and the enlarged cover 47 houses two air compressors 49, 50 driven by separate electric motors 51, 52 respectively. The top of the cap is formed with an opening 53 for entry of air into the cap and a filter 54 is mounted in an air-tight partition 55 between the opening 53 and the compressors, so that air for the motors is drawn through the filter. The output from the compressors is led through pipes 56, 57 extending through the extension piece 45 and into the support tube 10. The compressor 49 supplies air for the air injector 20 (FIG. 1), and the other compressor 50 supplies air for the shut-off valve 21. In operation, the compressor 49 is driven continuously while the compressor 50 is driven only during the periods when back-flushing or recalibration of the apparatus is required.

The apparatus described with reference to FIG. 1 would normally have a length such that water being tested by the apparatus would be drawn into the skirt at a level between 2 and 3 meters below the surface of the water. In a case in which the water to be tested has to be drawn from a much greater depth, for example 50 meters below the surface, the elbow joint can conveniently be replaced by a length of rubber or polyethylene tubing to enable the support tube, skirt and probe to be sunk to the required depth while the standpipe was held in a vertical position just below or projecting above the surface of the water. Injection of air into the water in the standpipe would then cause the water to rise in the standpipe and induce a flow of water into the skirt and up the polyethylene tubing into the standpipe. When the apparatus is used at such depths, the support pipe 10 could conveniently be removed, the cap 28 secured on the plate 13 by the locking ring 12, the cable 25 fed in an air-tight manner through an aperture in the plate 13 and then led through the stub tube 19, up the polyethylene tubing, and out the top end of the standpipe.

The apparatus is of course not restricted to testing the oxygen content of water, but can be fitted with any suitable probe and used to test a property of a liquid responsive to the probe.

What we claim is:

1. A method of measuring a property of liquid in a storage tank, reservoir or river by means of an electro-chemical probe adapted when immersed in the liquid to provide an electrical signal representative of said property of the liquid, comprising locating said probe in an open-ended duct having at least a portion thereof immersed in the liquid and extending continuously upwards towards one end of the duct, injecting into said portion of the duct a gaseous fluid having known properties to which said probe is responsive, the gaseous fluid rising up the said portion of the duct and thereby entraining the liquid in the duct and discharging the liquid through said one end of the duct to cause a continuous stream of the liquid to flow past the probe, the point of injection of said gaseous fluid into the duct being downstream of the probe relative to the direction of flow of liquid through the duct, periodically closing said one end of the duct while continuing injection of said gaseous fluid, so that the gaseous fluid displaces the liquid around said probe and the gaseous fluid comes into contact with the probe, and then co-relating the output of the probe with the known properties of the gaseous fluid to calibrate the apparatus.

2. A method as claimed in claim 1 wherein the probe is responsive to the dissolved oxygen content in the liquid, and the gaseous fluid injected into the duct is air.

3. Apparatus for measuring a property of liquid in a storage tank, reservoir or river, comprising a housing adapted to be at least partially immersed in the liquid, said housing having an internal cavity and inlet and outlet openings communicating with said cavity, said inlet opening permitting entry of liquid into the cavity upon immersion of the housing with said cavity below the surface of the liquid, an electro-chemical probe mounted in said cavity and providing an electrical signal representative of a property of the liquid in the cavity, electrical conductor means for transmitting said signal to a terminal above the surface of the liquid, a standpipe having the lower end thereof connected to said outlet opening to receive liquid from said cavity, the upper end of the standpipe being adjacent the surface of the liquid upon immersion of the housing, conduit means connected to a supply of gas under pressure and opening into said standpipe intermediate the ends thereof, whereby gas discharged into the standpipe from the conduit means rises up the standpipe and entrains the liquid therein to cause the liquid to discharge out of the upper end of the standpipe and thereby cause a continuous flow of liquid through the cavity, and valve means mounted on the upper end portion of said standpipe and operable to close the standpipe, whereby continued injection of gas into the standpipe through said conduit means causes back-flushing of the liquid in the standpipe out through the cavity, and permits calibration of the apparatus against known properties of the gas to which the probe is responsive.

4. Apparatus as claimed in claim 3, wherein said housing comprises a vertical support tube, a skirt on the lower end of the support tube, and a sealing plate between the lower end of the tube and the skirt and closing off the lower end of the tube, the interior of the skirt forming said cavity, the wall of the skirt having an aperture therein forming said outlet opening, the sealing plate having an aperture through which the electro-chemical probe extends as a liquid tight fit, and said electrical conductor means extending upwards through said support tube, and wherein said valve means comprises a body having a valve chamber, and a flexible tube mounted in the valve chamber and forming a section of said standpipe, said flexible tube being collapsible to block flow of liquid therethrough upon supply of fluid to the chamber, said apparatus including two air compressors mounted in said support tube and each driven by a separate electric motor, one of said compressors supplying air under pressure to said conduit means opening into the standpipe, second conduit means extending between the second air compressor and said valve chamber to provide air under pressure for collapsing the flexible tube, and control means for controlling operation of the compressors.

* * * * *